United States Patent [19]

Soehngen et al.

[11] 4,257,997
[45] Mar. 24, 1981

[54] SOLVENT STRETCH PROCESS FOR PREPARING A MICROPOROUS FILM

[75] Inventors: John W. Soehngen, Berkeley Heights; Kenneth Ostrander, Summit, both of N.J.

[73] Assignee: Celanese Corporation, New York, N.Y.

[21] Appl. No.: 44,801

[22] Filed: Jun. 1, 1979

[51] Int. Cl.$^3$ .............................................. B28B 11/16
[52] U.S. Cl. .................... 264/145; 264/154; 264/288.8; 264/289.3; 264/DIG. 47
[58] Field of Search .............. 264/DIG. 47, 145, 154, 264/288.8, 289.3

[56] References Cited

U.S. PATENT DOCUMENTS

| 2,823,421 | 2/1958 | Scarlett | 264/216 |
| 3,725,520 | 4/1973 | Suyuki et al. | 264/41 |
| 3,813,461 | 5/1974 | Murayama et al. | 264/41 |
| 3,839,516 | 10/1974 | Williams et al. | 264/41 |
| 4,138,459 | 2/1979 | Brayinsky et al. | 264/DIG. 47 |
| 4,153,751 | 5/1979 | Schwarz | 264/154 |
| 4,176,148 | 11/1979 | Magder et al. | 264/154 |

Primary Examiner—Maurice J. Welsh
Attorney, Agent, or Firm—Kenneth A. Genoni

[57] ABSTRACT

The present invention provides an improvement in a "solvent stretch" process which renders it possible to transverse stretch a microporous film prepared from a precursor film which has been previously uniaxially stretched in a direction perpendicular to the intended transverse stretching direction to thereby improve the permeability of the microporous film while also improving the balance of mechanical properties thereof in both directions of stretch.

The improvement lies in uniaxially stretching the precursor film to form a microporous film having a specifically defined permeability as measured by the Gurley test. The requisite permeability of the uniaxially stretched microporous film is obtained by selecting the polymer employed to prepare the precursor film based on certain specifically defined property requirements and by employing specifically defined process conditions during uniaxial stretching. The uniaxially stretched microporous film having the requisite permeability can then be transverse stretched under certain conditions without the likelihood of developing splits or breaks in the biaxially stretched microporous film.

27 Claims, 2 Drawing Figures

SOLVENT STRETCH PROCESS FOR PREPARING A MICROPOROUS FILM

BACKGROUND OF THE INVENTION

1. Field of the Invention

The present invention relates to an improvement in the "solvent stretch" process for preparing a microporous film.

2. Description of the Prior Art

Williams et al U.S. Pat. No. 3,839,516 discloses a process, herein referred to as the "solvent stretch" process, for preparing microporous films from a suitable precursor film having at least two components, e.g., an amorphous component and a crystalline component. The precursor film is typically contacted with a swelling agent and longitudinally stretched greater than its original length while still in contact with the swelling agent and then, while the film is in the stretched state, the swelling agent is removed.

Notwithstanding the broad descriptive language of this patent, it has heretofore been generally assumed that multidirectional stretching, of the precursor film described therein, in the presence or absence of a swelling agent, would cause many processing difficulties such as tearing of the microporous film.

Porous films which are prepared from a process which includes a biaxial stretching step are well known in the art as illustrated by U.S. Pat. Nos. 2,823,421; 3,725,520; and 3,813,461. The processes described in these patents, however, do not employ a "solvent stretch" process as described herein and are therefore not concerned with alleviating the particular problems peculiar to such process.

Consequently, there has been a continuing search for a method of achieving an improvement in the balance of the mechanical properties of a "solvent stretched" microporous film, such as tensile strength and tear strength, which would result from biaxially stretching a precursor film employed therein. There has also been a continuing effort to improve the permeability of a microporous film prepared in accordance with the "solvent stretch" process. The present invention has been developed in response to this search.

It is an object of the present invention to enhance the permeability porosity, and surface area, and improve the balance of mechanical properties in both the machine and cross machine directions of a microporous film prepared in accordance with the "solvent stretch" process described herein.

These and other objects and features of the invention will become apparent from the claims and from the following description when read in conjunction with the accompanying drawings.

SUMMARY OF THE INVENTION

Inn one aspect of the present invention there is provided an improved process for preparing an open-celled microporous film by (1) contacting a non-porous precursor film having both an amorphous component and a crystalline component with a swelling agent comprising a non-aqueous solvent having a Hildebrand solubility parameter at or near that of the precursor film, for a time sufficient to permit adsorption of the swelling agent into the film, (2) stretching said precursor film in at least one direction while in contact with the swelling agent, and (3) removing said swelling agent while maintaining said film in its stretched state. The improvement in said process comprises:

(a) providing said precursor film from an olefin homopolymer or mixtures thereof characterized by a balance of properties of density, melt index, molecular weight distribution ratio ($\overline{M}_w/\overline{M}_n$), crystallization time, and a average gel count, sufficient to impart to the non-porous precursor film the potential to develop a Gurley value of less than about 2 seconds per mil of film thickness when stretched in a uniaxial direction in accordance with step (b);

(b) uniaxially stretching the precursor film of (a) while in contact with the swelling agent under conditions of degree of stretch, strain rate, temperature, and precursor film thickness, which are controlled in a manner sufficient to yield a uniaxially stretched microporous film having a Gurley value of less than 2.0 seconds per mil of film thickness; and (c) transverse stretching the microporous film of (b) in a direction perpendicular to the uniaxial direction of stretch to increase the permeability of the microporous film of (b) without causing splitting of the resulting biaxially stretched microporous film.

The solvent stretched film when trasverse stretched, exhibits a reduced tendency to split and the resulting biaxially stretched microporous film exhibits an improvement (i.e., substantially equal balance) in the mechanical properties in both directions of orientation induced by said biaxial stretching and also an improvement in liquid and gas permeability.

DESCRIPTION OF THE PREFERRED EMBODIMENTS

Figure 1:
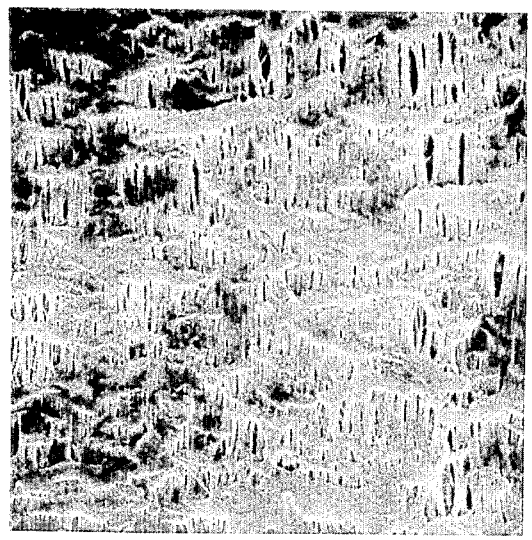
FIG. 1 is a scanning electron micrograph of a uniaxially "solvent stretched" polyethylene microporous film at a magnification of 5,000.

The present invention provides an improvement in the basic "solvent stretch" process disclosed in U.S. Pat. No. 3,839,516 wherein a microporous film having certain defined characteristics which has been prepared generally in accordance therewith, but with certain critical improvements, by uniaxially stretching a precursor film, is additionally stretched in a direction perpendicular, i.e., transverse, to the uniaxial direction of stretch under controlled conditions of temperature, rate and degree of extension. The critical improvements in the basic uniaxial "solvent stretching" process reside in the selection of certain process conditions which are critical to obtain a uniaxially "solvent stretched" microporous film which is capable of being subsequently transverse stretched.

It is to be understood in characterizing the microporous films of the present invention that porous or cellular films can be classified into two general types: one type in which the pores are not interconnected, i.e., a closed-cell film, and the other type in which the pores are essentially interconnected through more or less tortuous paths which may extend from one exterior surface or surface region to another, i.e., an open-celled film. The porous films of the present invention are of the latter type.

Further, the pores of the product of the present invention are microscopic, i.e., the details of the pore configuration or arrangement are discernible only by microscopic examination. In fact, the open cells or pores in the films are smaller than those which can be measured using an ordinary light microscope, because the wave length of visible light, which is about 5000 Angstroms (an Angstrom is one ten-billionth of a meter), is longer than the longest planar or surface dimension of the open cell or pore. The microporous films produced by the present invention may be identified, however, by using electron microscopy techniques which are capable of resolving details of pore structure below 5000 Angstroms.

The microporous films produced by the present invention are also characterized by a reduced bulk density, sometimes hereinafter referred to simply as a "low" density. The bulk density is also a measure of the increase in porosity of the films. That is, these microporous films have a bulk or overall density lower than the bulk density of corresponding film composed of identical polymeric material but having no open-celled or other voidy structure. The term "bulk density" as used herein means the weight per unit of gross or geometric volume of the film, where gross volume is determined by immersing a known weight of the film in a vessel partly filled with mercury at 25° C. and atmospheric pressure. The volumetric rise in the level of mercury is a direct measure of the gross volume. This method is known as the mercury volumenometer method, and is described in the *Encylopedia of Chemical Technology*, Vol. 4, page 892 (Interscience 1949).

The basic "solvent stretch" process as referred to herein upon which the present invention improves may be summarized by the following:

(a) contacting a polymeric non-porous precursor film, comprising a crystalline polymer having both an amorphous and a crystalline component, with a swelling agent, said swelling agent comprising a non-aqueous solvent having a Hildebrand solubility parameter at or near that of the polymeric film, for a time sufficient to permit absorption of the swelling agent into the film;

(b) stretching said precursor film in at least one direction while in contact with the swelling agent; and (c) removing the swelling agent from the film while maintaining said film in its stretched state.

In accordance with the well known principles of the basic "solvent stretch" process the precursor film to be used must contain at least two components one of which has a greater affinity for the chosen swelling agent than the other components. Preferably crystalline materials which have both an amorphous component and a crystalline component lend themselves readily to the basic solvent "stretch process". Details of the mechanism by which the basic "solvent stretch" process achieves microporosity are provided in the above-described patent and need not be discussed in any detail.

The broad general requirements of the crystalline polymer used to prepare the precursor film employed in the basic "solvent stretch" process of the prior art is that they must have a percent crystallinity of at least 30 percent, preferably at least 40 percent, and most preferably at least 50 percent, e.g., about 50 to 90 percent, or more. Percent crystallinity is determined by the X-ray method described by R. G. Quynn et al, in the *Journal of Applied Polymer Science*, Vol. 2, No. 5, pp. 166–173 (1959). For a detailed discussion of crystallinity and its significance in polymers, see *Polymers and Resins*, Golding (D. Van Nostrand, 1959).

A significant group of polymers, i.e., synthetic resinous materials, to which the basic "solvent stretch" process may be applied are the olefin polymers, e.g., polyethylene, polypropylene, poly-3-methyl butene-1, poly-4-methyl pentene-1, as well as copolymers of propylene, 3-methyl butene-1, 4-methyl pentene-1, or ethylene with each other or with minor amounts of other olefins, e.g., copolymers of propylene and ethylene, copolymers of a major amount of 3-methyl butene-1 and a minor amount of a straight chain n-alkene such as n-octene-1, n-hexadecene-1, n-octadecene-1, or other relatively long chain alkenes, as well as copolymers of 3-methyl pentene-1 and any of the same n-alkenes mentioned previously in connection with 3-methyl butene-1. These polymers in the form of films should generally have a percent crystallinity of at least 30 percent, preferably at least 40 percent, and most preferably about 50 percent to 90 percent, or higher.

For example, a film-forming homopolymer of polyethylene or polypropylene may be employed. When polyethylene is used a linear polymer is preferred having a weight average molecular weight between 50,000 and 800,000 preferably between 50,000 and 500,000. When propylene homopolymers are contemplated, it is preferred to employ an isotatic polypropylene having a percent crystallinity as indicated above, a weight average molecular weight ranging from about 50,000 to 750,000 preferably about 200,000 to 500,000 and a melt index (ASTM-1958D-1238-57T, Part 9, page 38) from about 0.1 to about 75, preferably about 0.5 to 30, so as to give a final film product having the requisite physical properties.

As is discussed hereinafter, certain of the above requirements have been modified and additional requirements have been identified which provide a basis for selecting the appropriate olefin polymer from the numerous polymers described above which are to be employed in preparing a precursor film which is capable of being biaxially stretched in accordance with the present invention.

The swelling agent should be such that it preferentially swells at least one of the minor components of the bicomponent or multicomponent film. For most polymers solvent stretching can be conducted by contact with any one of a number of suitable solvents.

Generally, a solvent having a Hildebrand solubility parameter at or near that of the polymer would have a solubility suitable for the drawing process described herein. The Hildebrand solubility parameter measures the cohesive energy density. Thus, the underlying principle relies on the fact that a solvent with a similar cohesive energy density as a polymer would have a high affinity for that polymer and would be adequate for this process.

General classes of swelling agents from which one appropriate for the particular polymeric film may be chosen are lower aliphatic alcohols such as ethanol, etc.; lower aliphatic ketones such as acetone, methyl ethyl-ketone cyclohexanone; lower aliphatic acid esters such as ethyl formate, butyl acetate, etc.; halogenated hydrocarbons such as carbon tetrachloride, trichloroethylene, perchloroethylene, chlorobenzene, etc.; hydrocarbons such as heptane, cyclohexane, benzene, xylene, tetraline, decaline, etc.; nitrogen-containing organic compounds such as pyridine, formamide, dimethylformamide, etc.; ethers such as methyl ether, ethyl ether, dioxane, etc. A mixture of two or more of these organic solvents may also be used.

The preferred swelling agents for polyethylene include perchloroethylene (BP 127° C.) and trichloroethylene (B.P. 86° C.).

The types of apparatus suitable for forming the precursor films employed in the present invention are well known in the art.

For example, a conventional film extruder equipped with a shallow channel metering screw and coat hanger die, is satisfactory. Generally, the resin is introduced into a hopper of the extruder which contains a screw and a jacket fitted with heating elements. The resin is melted and transferred by the screw to the die from which it is extruded through a slit in the form of a film from which it is drawn by a take-up or casting roll. More than one take-up roll in various combinations or stages may be used. The die opening or slot width may be in the range, for example, of about 10 to 200 mils.

Using this type of apparatus, film may be extruded at a drawdown ratio of about 5:1 to 200:1, preferably 10:1 to 50:1.

The terms "drawdown ratio" or, more simply, "draw ratio", as used herein is the ratio of the film wind-up or take-up speed to the speed of the film issuing at the extrusion die.

The melt temperature for film extrusion is, in general, no higher than about 100° C. above the melting point of the polymer and no lower than about 10° C. above the melting point of the polymer.

For example, polypropylene may be extruded at a melt temperature of about 180° C. to 270° C. preferably 200° C. to 240° C. Polyethylene may be extruded at a melt temperature of about 175° to about 225° C. or higher.

The extrusion operation is preferably carried out with slow cooling in order to minimize stress and any associated orientation which might result from a fast quench to obtain maximum crystallinity but yet fast enough to avoid developing large spherulites. This may be accomplished by controlling the distance of the chill roll take-up from the extrusion slit.

While the above description has been directed to slit die extrusion methods, an alternative method of forming the starting films contemplated by this invention is the blown film extrusion method wherein a hopper and an extruder are employed which are substantially the same as in the slit die extruder described above. From the extruder, the melt enters a die from which it is extruded through an annular orifice to form a tubular film having an initial diameter $D_1$. Air enters the system through an inlet into the interior of said tubular film and has the effect of blowing up the diameter of the tubular film to a diameter $D_2$. Means such as air rings may also be provided for directing the air about the exterior of extruded tubular film so as to provide different cooling rates. Means such as a cooling mandrel may be used to cool the interior of the tubular film. After a distance during which the film is allowed to completely cool and harden, it is wound up on a take-up roll.

Optionally, the extruded film may then be initially heat treated or annealed in order to improve crystal structure, e.g., by increasing the size of the crystallites and removing imperfections therein. Generally, this annealing is carried out at a temperature in the range of about 5° C. to 100° C. below the melting point of the polymer for a period of a few seconds to several hours, e.g., 5 seconds to 24 hours, and preferably from about 30 seconds to 2 hours. For polyethylene, the preferred annealing temperature is about 100° to 120° C.

In accordance with the generally accepted principles of the basic "solvent stretch" process the extruded precursor film, which can be optionally and preferably annealed, is swollen in contact with a swelling agent, preferably immersed therein, and stretched uniaxially while still in contact with the swelling agent. The swelling agent is removed preferably by evaporation, while under tension, and preferably at the same extension.

The above steps can be accomplished by passing the precursor film between a first pair of rolls through the swelling agent and then through a second pair of rolls. The second pair of rolls are rotated at higher peripheral speeds than the first pair of rolls so as to effect stretching of the film to a predetermined extent. If stretching is to be achieved in multiple steps, several sets of rolls can be employed as well as several different immersion baths of the swelling agent.

It has been found that certain factors (i.e., processing parameters) employed in the preparation of the uniaxially stretched microporous films by the basic "solvent stretch" process must be controlled within certain limits to reduce the tendency of a uniaxially "solvent stretched" microporous film to split when subsequently stretched in a transverse direction.

The first of these factors is the Gurley value (ASTM D-726) of the uniaxially solvent stretched microporous film. It has been found that uniaxially "solvent stretched" microporous film as described herein which is to be subsequently transverse stretched must exhibit a Gurley value of less than 2.0 seconds, preferably less than about 1.8 seconds (e.g., 1.5 seconds), and most preferably less than about 1.0 second per mil of film thickness of the uniaxially solvent stretched film or lower.

As is well known, the Gurley test is an indication of the air permeability of the microporous film which in turn reflects the porosity of the film. Gurley values are inversely related to permeability. Thus, it is believed that the more permeable the uniaxially stretched microporous film is the more readily deformable it will be when stretched in the transverse direction and consequently the lower the probability that splits and abrupt breaks will develop upon transverse stretching. If the Gurley value of the uniaxially "solvent stretched" microporous film exceeds about 2.0 seconds per mil of film thickness the microporous film will generally split or tear when additionally stretched in a transverse direction.

There are several process conditions which have been found to affect the permeability and porosity of the uniaxially "solvent stretched" microporous films to lower the Gurley values to within the limits described above. Such conditions include the identity of the polymer, degree of stretch or extension, strain rate, temperature of the swelling agent during "solvent stretching", and thickness of the precursor film.

More specifically, it has been found that the identity of the polymer or mixtures thereof which is employed to prepare the precursor film is a critical factor to be controlled to achieve a uniaxially "solvent stretched" microporous film exhibiting the required Gurley values described herein.

The selection of the appropriate polymer is determined on the basis of a number of different polymer properties which each contributes toward lowering the Gurley value of the uniaxially "solvent stretched" microporous film. These polymer properties include molecular weight distribution ratio ($\overline{M}_w/\overline{M}_n$), melt index (ASTM D-1238), density (e.g., the polymer should be a homopolymer) and crystallization time.

The selection of a suitable homopolymer for use in a solvent stretch process on the basis of melt index and molecular weight distribution ratio is detailed in U.S. patent application Ser. No. 44,805, filed June 1, 1979, of John Soehngen entitled "Improved Solvent Stretch Process for Preparing Microporous Films from Precursor Films Having Controlled Crystalline Structure" the disclosure of which is herein incorporated by reference.

Thus, in accordance with the above application olefin polymers (i.e., those polymers prepared by polymerization of olefin monomers through their unsaturation) such as polyethylene having a high melt index, i.e., not less than about 3 and preferably from about 3 to about 20 (i.e., in the absence of nucleating agents) are preferred to prepare the precursor films of the present invention which exhibit a higher permeability potential when employed in a "solvent stretch" process. The lower limit of the melt index, i.e., about 3, can be reduced further to about 0.3 by employing nucleating agents which compensate for the effect of employing lower melt indices below about 3 and for the tendency of certain polymers to form large spherulites. Also, the olefin polymer as defined therein having a broad molecular weight distribution ratio ($\overline{M}_w/\overline{M}_n$) of not less than about 3.8, typically from about 3.8 to about 13 and preferably from about 6 to about 12 (e.g. about 8 to about 12) will generally exhibit a higher permeability potential when employed to prepare precursor films for use in the "solvent stretch" process.

Similarly, it is preferred to employ olefin homopolymers having as high a density as technically possible rather than co-polymers in preparing the precursor film since the use of homopolymers of increasingly higher density improves the morphological structure of the microporous films prepared therefrom. When polyethylene is employed as the polymer used to prepare the precursor film the density thereof should not be less than about 0.960 gm/cc, preferably from about 0.960 to about 0.965 gm/cc, and most preferably from about 0.962 to about 0.965 gm/cc. These density ranges are indicative of polyethylene homopolymers. The term density as used herein is defined as the value in gm/cc obtained by performing ASTM D-1505 on a particular polymer.

A functional relationship has also been found to exist between the crystallization time of the polymer and permeability potential. The crystallization time is determined by heating the polymer to a temperature of above the melting point (e.g., 200° C. for polyethylene) and held at that temperature for one minute. The polymer is then allowed to cool to a predetermined temperature (i.e., 120° C. polyethylene) and held at this temperature while the time it takes for crystallization to occur is determined by differential scanning calorimerity (DSC). In the DSC analysis a plot is made of the heat evolved during crystallization as a function of time. The time it takes for the DSC curve to peak is taken as the crystallization time.

Polymers having increasingly lower crystallization times will generally exhibit increasingly higher permeability potentials. Crystallization times for polyethylene to reach the DSC peak at a temperature of 120° C. should be less than about 70 seconds and preferably from about 10 to about 40 seconds.

It should be understood that olefin polymers, particularly polyethylene, which possess one or more of the above described properties outside the ranges described herein, can be employed in a "solvent stretch" process. However, a penalty is paid in terms of a decreasingly lower permeability of the resulting uniaxially "solvent stretched" microporous film as any particular property increasingly deviates from the preferred polymer property ranges. In short, it is required only that the balance of the abovedescribed properties as a whole of the chosen polymer be such that a precursor film prepared therefrom possesses the potential to exhibit Gurley values within the range described above when uniaxially stretched in accordance with the improved "solvent stretch" process described herein.

For example, the effect of a polymer having a broad molecular weight distribution ratio can offset to some extent the effect of decreased melt index (i.e., higher molecular weight) or lower density. Moreover, polymers having different sets of properties can be mixed to yield a blend having the requisite overall balance of properties.

The most preferred resins, however, will comprise a high melt index, high density, quickly crystallizing homopolymer having a broad molecular weight distribution ratio.

The preferred homopolymer for use in the improved "solvent stretch" process is polyethylene.

The degree of stretch in the swelling agent is another factor which affects the Gurley level of the uniaxially "solvent stretched" microporous film. It has been found that increasing the degree of stretch of the precursor film up to about 300 percent of the original length of the precursor film increases the permeability of the uniaxially "solvent stretched" microporous film. When the precursor film is "solvent stretched" to increasingly higher levels beyond about 300 percent of its original length, the effect on permeability levels off and eventually decreases as the Gurley values increase rapidly to unacceptable levels. Thus, the degree of uniaxial stretch in the presence of a swelling agent should not exceed about 350% and can vary from about 70 to about 300%, and preferably from about 100 to about 300% (e.g. 300%) based on the original linear film dimension measured in the direction of stretch of the precursor film.

Another factor to be controlled in achieving a uniaxially "solvent stretched" microporous film having suitable Gurley values is the strain rate i.e., the rate at which the precursor film is stretched in the presence of the swelling agent. Thus it has been found that the lower the strain rate employed during uniaxial stretching of the precursor film the lower will be the Gurley values of the resulting microporous film. The strain rate is expressed as the percentage of stretch per unit time and is dependent in part upon the total degree of stretch. Thus, when a degree of stretch of from about 70 to about 300% is employed in stretching the precursor film, suitable strain rates can vary from about 5 to about 100%/minute and preferably from about 5 to about 20%/minute.

At the preferred degree of stretch of about 300% the preferred strain rate is about 15%/minute.

The strain rate can be increased by annealing the precursor film at constant length before contact with the swelling agent. Annealing of the precursor film permits it to respond to given "solvent stretch" conditions in a shorter period of time than would otherwise be obtained in the absence of annealing. Thus, although the minimum Gurley levels obtainable are not shifted to a lower limit they are obtainable within a shorter stretch time, i.e., higher strain rate. Suitable annealing temperatures when performed in-line, i.e. on a continuous basis, can vary from about 90° to about 120° C. and preferably from about 110° to about 120° C., for a period of time of which can vary from about 1 to about 30 minutes and preferably from about 2 to about 10 minutes (e.g., 5 minutes). Batch annealing of a large roll of precursor film (e.g. about 250 feet) will require longer periods, e.g. about 24 to 96 hours, at temperatures of from about 80° to about 90° C. to achieve similar results.

It is appropriate to mention that annealing duration and annealing temperature are generally interchangeable to a certain degree in the sense that the annealing temperature may be increased if the exposure thereto is decreased appropriately.

A process condition related to strain rate which, although not decreasing the mininum Gurley values exhibited by the uniaxially "solvent stretched" microporous film, increases the efficiency of the subsequent stretching operation is the web speed, i.e., the speed at which the precursor film passes through the swelling agent during solvent stretching. It has been found that the success of the solvent stretching process in terms of the permeability of the resulting uniaxially stretched microporous film is a function of the extent to which the swelling agent diffuses into the microporous film. Consequently the web speed is a function of the web path distance, i.e. the distance traveled by the precursor film while "solvent stretching" takes place. Consequently, the web speed can be increased by increasing the web path distance. The web path distance is efficiently increased by conducting the "solvent stretching" operation in multiple stages wherein the total degree of stretch described herein is achieved in incremental steps. In a preferred embodiment, the total web path distance can vary from about 120 to about 190 inches (e.g. about 190 inches). This distance is divided into 4 stretching zones. Each stretching zone is isolated by stretch rolls capable of stretching the precursor film a substantially equal portion of the total degree of stretch (e.g. 300%). By this method web speeds of about 1 to about 40 feet/minute (e.g. 40 feet/minute) may be employed.

Similarly, to aid diffusion of the swelling agent it is preferred to pre-soak the precursor film in the swelling agent at about the intended "solvent stretch" temperature for a period of about 10 seconds to about 10 minutes, and preferably for about 15 seconds to about 3 minutes, at substantially constant length (i.e., not greater than about 5% shrinkage or extension based on the original precursor film length).

The temperature of the swelling agent during uniaxial "solvent stretching" (i.e. solvent stretch temperature) is also controlled to achieve acceptable Gurley levels. The particular temperature employed during solvent stretching is dependent primarily on the boiling point of particular swelling agents, the degree of stretch and the strain rate employed. Generally "solvent stretch" temperature is directly related to permeability and will vary depending on the swelling agent employed. As the temperature of the swelling agent is increased, however, the precursor film becomes increasingly more swollen and the polymer chains begin to separate. If the "solvent stretch" temperature is raised too high (e.g. greater than about 95° C. for perchloroethylene) the polymer will swell to such an extent that the precursor film will split when uniaxially stretched. If the temperature employed during "solvent stretching" is too low, (e.g., below about 80° C. for perchloroethylene), unacceptable Gurley levels for purposes of transverse stretching are exhibited by the uniaxially stretched microporous film. Thus, the temperature during "solvent stretch" is controlled for each solvent in conjunction with the other process parameters disclosed herein to avoid extensive swelling and to achieve a microporous film exhibiting suitable Gurley levels, as described herein.

Typically, the solvent stretch temperature can vary from about 80° to about 95° C. and most preferably from about 85° to about 90° C.

When perchloroethylene is employed as the swelling agent, the degree of stretch employed is from about 70 to about 300% (e.g., 300%), and the strain rate is from about 5 to about 100%/minute (e.g., 15%/minute), the temperature during "solvent stretching" can vary from about 80° to about 95° C., and preferably from about 90° to 95° C. (e.g. 90° C.). When trichloroethylene is employed as the swelling agent under similar conditions the temperature will typically vary from about 25° to about 80° C. (e.g. 70° C.). After uniaxially "solvent stretching", the resulting precursor film is preferably allowed to cool to room temperature prior to transverse stretching.

The thickness of the precursor film is believed to be limited in part by the increasing difficulty of uniformly cooling a precursor film of increasingly greater thickness. Uneven cooling of the precursor film after preparation thereof is believed to lead to uneven crystallization between the film surface and film interior. Slower cooling of the polymer at the interior of the precursor film in turn causes large spherulites to develop therein. The presence of large spherulites in the precursor film not only decreases the permeability (i.e. increases Gurley values) of the resulting uniaxially "solvent stretched" microporous film but also creates stress points within the microporous film which contribute to splitting thereof during transverse stretching.

Precursor films prepared by slit die extrusion methods can typically be more uniformly cooled than those films prepared by blown film extrusion methods. Consequently, when the precursor film is prepared by slit die extrusion methods, the film thickness can be controlled to be as high as about 20 mils, typically from about 0.75 to about 15 mils (e.g. about 2 to 10 mils) and preferably from about 0.75 to about 6 mils and yet still achieve a uniaxially "solvent stretched" microporous film which exhibits acceptable Gurley values.

Alternatively, when the precursor film is prepared by blown film extrusion methods the film thickness is controlled to be about 0.75 to about 12 mils and preferably from about 0.75 to about 5 mils (e.g. about 1 to about 3 mils).

Generally, the thinner the film the more even the cooling which yields a uniaxially "solvent stretched" microporous film of higher permeability and more uniform porosity. However, for certain applications thicker microporous films may be required which would necessitate thicker precursor films.

An additional factor is to be considered when employing precursor films of increasingly greater thickness in the "solvent stretch" process. The permeability development of the uniaxially "solvent stretched" film appears to be rate dependent on diffusion of the swelling agent into the precursor film. Consequently, thicker films require longer periods of contact in the swelling agent. Therefore, the strain rate should be decreased in proportion to the thickness of the precursor film to achieve maximum permeability.

The permeability of the uniaxially "solvent stretched" microporous film can be further improved by post-soaking the "solvent stretched" microporous film in the swelling agent subsequent to uniaxial stretching, prior to transverse stretching at temperatures close to the solvent stretching temperature, e.g., about 70° to about 90° C. for periods of about 10 seconds to about 10 minutes while maintaining the film at substantially constant length (i.e., not greater than about 5% shrinkage or extension based on initial uniaxial "solvent stretched" film length).

It is to be understood that each of the above described process conditions which affect permeability are considered critical not in isolation by themselves, but as they interact together to achieve an overall balance of properties capable of yielding a uniaxially "solvent stretched" microporous film having the requisite permeability.

It is recognized that to an extent, there can be a trade-off where certain more preferred process conditions are selected to compensate for other less preferred conditions which are employed.

A second factor which can be controlled to prepare the uniaxially "solvent stretched" microporous films of the requisite permeability is gel formation. The presence of gels in the microporous film during transverse stretching is believed to localize stress therein which contributes to splits in the microporous film. Gel formation can be avoided by melt filtering the polymer employed to prepare the precursor film. This is achieved by passing the resin employed to form the precursor film, while molten, from an extruder through a suitable filter such as a screen pack changer (e.g. 200×1200 mesh) or Dynalloy TM X-6 or X-7 filter (rated 15 and 20 microns respectively). Dynalloy TM X-6 and X-7 are grades of depth type filter media fabricated of sintered metal fibers manufactured by fluid Dynamics, Inc., of Cedar Knolls, N.J. The fiber media is mounted in a suitable filter holder device and positioned at the exit end of a melt extruder and before the precursor film forming die. For continuous operation the filter media is changed periodically by switching the melt flow through an alternate standby filter while changing the depleted filter.

The resin is melt filtered until it exhibits a low average gel count of not greater than about 2.0, and preferably from about 0 to about 1.0 per 90 sq. inch area of precursor film.

The average gel count of the resin after filtration is determined by examining a sample of the precursor film and visually counting the number of gels in a 90 sq. inch area of film.

The transverse stretching operation which imparts a biaxial orientation to the microporous film can be performed in a number of different sequences in the presence of preferably in the absence of the swelling agent.

In a preferred embodiment the uniaxially "solvent stretched" microporous film as it emerges from longitudinal stretching, referred to herein as stretching in the machine direction (MD), is dried at a temperature sufficient to evaporate the swelling agent (e.g., 25° to 50° C.) by any suitable apparatus such as a forced hot air oven and preferably cooled to room temperature if dried at a temperature higher than room temperature. The cool, dried film is then passed continuously through a transverse stretching zone composed of a tenter frame having a chain of tenter clips on both sides of the film. The tenter clips grasp the edges of the longitudinally stretched film and move outward perpendicular to the machine direction to stretch the film in the cross machine direction (i.e. XMD).

The degree of transverse stretch by the tenter is controlled to be from about 25 to about 200%, preferably from about 60 to about 150%, and most preferably from about 75 to about 125%, based on the initial cross machine linear dimension of the uniaxially "solvent stretched" film prior to the transverse stretching. The improvement in mechanical strength properties (e.g. tensile strength) in the cross machine direction levels off at a transverse stretch of about 75% and at this degree of stretch the ratio of the mechanical properties in the machine direction and the cross machine direction are about 1:1.

The strain rate or rate of transverse extension is controlled to be from about 20 to about 100%/minute, and most preferably from about 75 to about 100%/minute. The temperatures of the microporous film during transverse stretching can vary from about 25° C. (e.g. room temperature) to about 100° C. It has been found that stretching at room temperature permits higher transverse stretch levels to be achieved than is possible at higher temperatures approaching 100° C. It should be noted however that it has also been found that at increasingly higher degrees of transverse stretch the Gurley value of the film levels off and may even result in an increase thereof (i.e. decrease in permeability) as the pores become more slit-like in the transverse direction. Consequently, the particular temperature selected within the above described range is not critical. Notwithstanding the above it is preferred to transverse stretch at room temperature since it is believed stretching at this temperature avoids crystallization during stretch and thereby provides a means whereby a more stable (e.g., reduced splitting and tearing of the film) stretch can be maintained in the tenter.

The thickness of the uniaxially stretched microporous film which is to be transverse stretched is for the most part dependent on the thickness of the precursor film as described herein, which in turn is limited by the Gurley value requirements placed on the uniaxially "solvent stretched" microporous film. Thus, generally any uniaxially "solvent stretched" microporous film which has the requisite permeability as defined herein may be transverse stretched without giving consideration to its thickness.

Transverse stretching may also be achieved on a batch basis using a Bruckner TM stretching frame. The stretch mode of a Bruckner TM frame is different from that of a tenter frame in that no restraint is applied to the film in the machine direction. Consequently, shrinkage in the original machine direction (e.g. about 5 to about 50%) during transverse stretching occurs. This permits higher degrees of stretch to be utilized when employing this mode of stretch. When employing a Bruckner TM frame, therefore, the degree of stretch can be as high as 300% in the cross machine direction. Other processing conditions employed during transverse stretching with a Bruckner TM frame are similar to those employed with the tenter mode of stretching.

After the microporous film has been stretched in the transverse direction it is preferably annealed, i.e. heat set, at a temperature of from about 25° C. up to less than the fusion temperature and, typically from about 80° to about 140° C., and preferably from about 85° to about 100° C. to stabilize the microporous structure of the film against shrinkage at room temperature over a long period of time or when subjected to elevated temperatures.

The annealing is carried out while the film is being held under tension, in at least its cross machine direction and preferably in both the machine and cross machine directions, i.e. such that the film is not free to shrink or can shrink in either direction to only a controlled extent not greater than about 15 percent, but not so great a tension as to stretch the film more than an additional 15 percent in either direction based on the original linear dimensions of the biaxially stretched microporous film prior to annealing. Preferably, the tension is such that substantially no shrinkage or stretching occurs, e.g. less than 5 percent change in stretched length in either direction.

The duration of annealing which is carried out after the transverse stretching operation can vary from about 5 to about 180 seconds at the higher annealing temperatures and, in general, may be within the range of about 0.1 second to about 1 hour (about 5 seconds to about 1 hour) and preferably about 1 to 30 minutes.

Annealing can be effected in an atmosphere heated to the prescribed amount. Satisfactory performance can be had in hot-air circulating ovens located at the after-end of a stretcher frame. The ovens can be provided with differential speed rollers in order for the film to be maintained under longitudinal tension, i.e. tension in the machine direction, while being advanced at speeds designed to provide proper residence of the film within the annealing ovens. The prescribed lateral tension, i.e. tension in the cross machine direction, under which the films are to be maintained during post annealing can be provided for by the inclusion of a constant-width tenter-frame within the oven.

It is to be understood that, although the transverse stretching operation has been described in terms of the preferred embodiment which employs a sequential on line procedure of longitudinal (i.e. machine direction) "solvent stretch" -dry- transverse stretch, other sequences may also be employed. For example, an off-line procedure can be employed wherein subsequent to longitudinal stretching the uniaxially "solvent stretched" microporous film is wound up and transversely stretched at a later date. Moreover, it is not necessary to dry the uniaxially stretched microporous film prior to transverse stretching nor is it necessary to remove the uniaxially stretched microporous film from contact with the swelling agent before transvere stretching.

In another embodiment the microporous film may be stretched in the transverse direction (i.e. cross machine direction) in the presence of a swelling agent, optionally dried and then stretched in the machine direction. In this embodiment, the uniaxial orientation is first imparted in the cross machine direction and the same requirement with respect to permeability as described herein for uniaxially solvent stretched microporous film must be fulfilled by controlling the process conditions also as described herein.

It should also be understood that the efficiency of the biaxial stretching process can be increased by feeding two or more ply rolls of film simultaneously into the solvent stretching apparatus.

The biaxial stretching process described herein substantially increases permeability of the resulting microporous films over the corresponding uniaxially "solvent stretched" film from which they are prepared.

The permeability of the microporous films of the present invention is determined by the Gurley test, i.e., according to ASTM D 726 by mounting a film having an area of one square inch in a standard Gurley densometer. The film is subject to a standard differential pressure (the pressure drop across the film) of 12.2 inches of water. The time in seconds required to pass 10 cm$^3$ of air through the film is an indication of permeability.

Improvements of about 200 to about 300% in permeability relative to the uniaxially "solvent stretched" microporous film can be obtained. Thus, the biaxially stretched microporous film prepared in accordance with the present invention exhibits a Gurley value of from about 1.5 to about 0.4 seconds, preferably from about 1.0 to about 0.4 seconds, and most preferably from about 0.7 to about 0.4 seconds per mil of film thickness.

The improvement in permeability is achieved as a result of the transverse stretching procedure. It is believed that transverse stretching changes the size of the pores of the uniaxially "solvent stretched" microporous film by increasing their width and decreasing their length.

An appreciation of the effects of the transverse stretching operation may be obtained from an inspection of the figures.

FIG. 1 is a scanning electron micrograph of a uniaxially "solvent stretched" polyethylene microporous film which may be produced in accordance with the method of Example 1 employing perchloroethylene swelling agent, a degree of stretch in the machine direction of 300%, a strain rate of 38%/min., and a solvent stretch temperature of 95° C.

Figure 2:
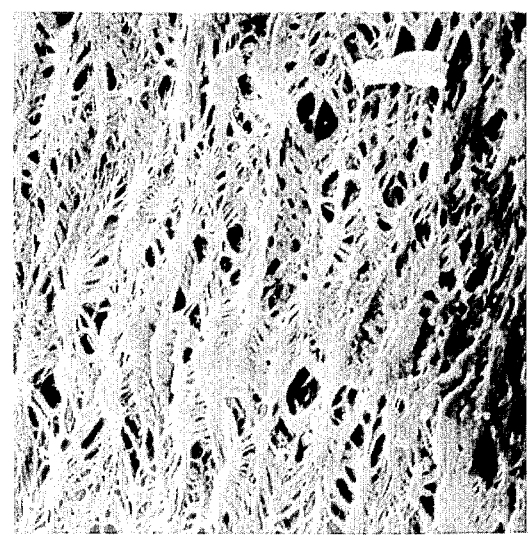
FIG. 2 is a scanning electron micrograph of a biaxially stretched polyethylene microporous film at a magnification of 5,000.

FIG. 2 is a scanning electron micrograph of a biaxially stretched polyethylene microporous film of the present invention which can be prepared in accordance with the method of Example 1 by employing (a) a degree of stretch of 300%, a strain rate of 38%/min. in the machine direction, and a "solvent stretch" temperature of 95° C., and (b) a degree of stretch of 96%, a strain rate of 300%/min., and a stretch temperature of 110° C. in the transverse (i.e. cross machine) direction.

FIGS. 1 and 2 are shown at a magnification of 5000.

Referring to FIG. 1, the microporous film shown therein has a plurality of elongated, non-porous, interconnecting surface regions or areas A which have their axis of elongation substantially parallel to each other, and substantially normal or perpendicular to the direction in which the film is stretched or drawn in the machine direction. Substantially alternating with and defined by the non-porous surface regions A are a plurality of parallel fibrils C. The fibrils C which appear white or whitish on the film are connected at each of their ends to the non-porous regions A and are substantially perpendicular to them. Between the fibrils C are the pores D which appear as dark longitudinal holes. The length (parallel to the machine direction of stretch) to width (perpendicular to the machine direction of stretch) ratio of these pores is from about 4:1 to about 6:1.

Referring to FIG. 2, the microporous film of the present invention shown therein has a plurality of elongated non-porous, interconnecting surface regions or areas A which have their axis of elongation substantially parallel to each other and substantially perpendicular to the machine direction. Substantially alternating with and defined by the non-porous surface region A is a plurality of parallel fibrils C. The fibrils C which appear white or whitish on the film are connected at each of their ends to non-porous regions A and are substantially oblique thereto. Between the fibrils C are the pores D which now appear as dark substantially circular holes wherein the ratio of the linear dimensions thereof in the machine and cross machine directions are substantially equal.

The above described micrographs were taken using the electron microscopy technique described in Geil's Polymer Single Crystals, page 69 (Intersciences 1963), and are considered as true reproductions.

Thus, it is believed that the increase in permeability is a result of a change in pore shape of the previously existing pores of the uniaxially "solvent stretched" microporous film caused by stretching in the transverse direction and not by the creation of new pores which does not appear to occur.

The porosity of the biaxially stretched microporous film of the present invention may be defined as a percent ratio of the total volume occupied by the void space of a standard sample of microporous film to the bulk volume of the same sample which is the sum of the void space volume and the volume occupied by the solid material of the film itself. The % porosity is determined by measuring the thickness, length and width of a microporous film sample to determine the film's bulk volume. The film sample is then weighed and the density of the film is determined. The density of the polymer resin used to prepare the film is then determined. The % porosity is then calculated from the equation:

$$\% \text{ Porosity} = \left(1 - \frac{\text{density of film sample}}{\text{density of resin}}\right) \times 100$$

The porosity of the microporous films prepared in accordance with the present invention may vary from about 40 to about 85%, preferably from about 50 to about 85%, and most preferably from about 60 to about 85%.

The biaxially stretched microporous films of the present invention, in a tensionless state, have a lowered bulk density compared with the density of corresponding polymeric materials having open-celled structure, e.g., those from which it is formed. Thus, the films have a bulk density no greater than 60% and preferably about 15 to about 50% of the precursor film. Stated another way, the bulk density is reduced by at least 40% and preferably about 60 to about 85%. The bulk density is also a measure of porosity, that is, where the bulk density is about 15 to 50 percent of the starting precursor film, the porosity has been increased by 50 to 85 percent because of the pores or holes.

The final crystallinity of the biaxially stretched microporous film is preferably at least 60 percent, more preferably at least 65 percent, and more suitably about 70 to 85 percent, as determined by the X-ray method by R. G. Quynn et al in the *Journal of Applied Polymer Science*, Vol. 2, No. 5, pp. 166-173. For a detailed discussion of crystallinity and its significance in polymers, see *Polymers and Resins*, Golding (D. Van Nostrand 1959).

The biaxially stretched microporous films of the present invention may also have an average pore size of about 1,000 to about 10,000 Å, and more typically about 2,000 to about 6,000 Å. These values are determined by mercury porosimetry as described in an article by R. G. Quynn et al, on pages 21–34 of *Textile Research Journal*, January, 1963 or by the use of electron microscopy as described in Geil's *Polymer Single Crystals*, p. 69 (Interscience 1963). The pore size is generally indicative of the narrowest dimension of the pore. Alternatively an electron micrograph can be employed and pore length and width measurements can be obtained by simply utilizing a ruler to directly measure the length and width of the pores on an electron micrograph magnified photograph taken usually at 5,000 to 10,000 magnification and scaling down to appropriate size.

The biaxially stretched microporous films will generally exhibit an average pore width by this method of about 2,000 to about 10,000, Å, preferably from about 4,000 to about 8,000 Å, and an average pore length of from about 2,000 to about 10,000 Å and preferably from about 4,000 to about 8,000 Å. Generally the pore length values obtainable by electron microscopy are approximately equal to the pore size values obtained by mercury porosimetry. The ratio of the pore length to width measurements will vary depending of the degree of stretch in the transversed section.

When the biaxially stretched microporous films of the present invention are prepared which exhibit the described Gurley values and porosity values, and a bulk density about 15 to 50 percent of the bulk density of the corresponding polymer film having no open-celled structure, the resulting films will also be found to have a surface area within certain predictable limits. This surface area value or characteristic is inherent in the films when they also have the Gurley value and reduced bulk density values given above. Thus, in the films of the present invention when Gurley values and bulk density values are indicated, they will also be found to have a surface area of at least 10 sq.m/gm., and preferably in the range of about 20 to 40 sq.m/gm. For films formed from polyethylene, the surface area generally ranges from about 10 to 40 sq.m/gm., and preferably about 35 sq.m/gm.

Surface area may be determined from nitrogen or krypton gas adsorption isotherms using a method and apparatus described in U.S. Pat. No. 3,262,319. The surface area obtained by this method is usually expressed as square meters per gram.

In order to facilitate comparison of various materials, this value can be multiplied by the bulk density of the material in grams per cc. resulting in a surface area quantity expressed as square meters per cc.

The resulting biaxially stretched microporous films of the present invention find application in areas wherever breathability and porosity superior to that of the prior art films is desired. For example, these films are useful in the preparation of barriers having increased moisture transmission rates such as clothing, sterile packaging, separation filters, battery separators, and the like. While the instant films do exhibit increased pore size they are still an effective barrier to most bacteria. In addition, the instant films are quite useful in areas where films are required to be exposed to heat with a maximum of shrinkage, i.e., sterilizable packaging.

The invention is additionally illustrated in connection with the following Examples which are to be considered as illustrative of the present invention. It should be understood, however, that the invention is not limited to the specific details of the Examples. All parts and percentages in the claims as well as the remainder of the specification are by weight unless otherwise specified.

EXAMPLE 1

A blend of crystalline polyethylene resins comprising 2.5%, by weight of the blend, of SOLTEX G 60-42 resin (which is employed as a nucleating agent) and 97.5%, by weight of the blend, of AMOCO 650 F4 resin is prepared by the blown film extrusion method to form a precursor film and allowed to cool. The appropriate properties of each of the resins of the blend is provided at Table I. The resulting precursor film which has a thickness of 2.7 mils, is annealed at constant length at 90° C. for 72 hours, then presoaked in perchloroethylene (B.P. 121° C.) at a temperature of 90° C. for about 15 seconds and subsequently stretched in perchloroethylene by passing the precursor film through a first pair of rolls, through an immersion bath of perchloroethylene and through a second pair of rolls which are rotated at a peripheral speed higher than the first pair of rolls and at a speed sufficient to obtain a degree of stretch of 300% in the machine direction and a strain rate of 215%/min. The temperature of the perchloroethylene immersion bath is maintained at 90° C. during stretching. The perchloroethylene is then removed by evaporation and the sample allowed to dry in air at room temperature in the stretched state. A few small samples of the film are tested as indicated at Table II run 1.

Several additional uniaxially stretched samples are each then placed in a Bruckner ™ stretch frame and stretched in air at 90° C. in a transverse direction, i.e. cross machine direction (XMD), at a strain rate of 300%/minute (for runs 2 to 5) and 500%/minute for run 6 to varying degrees of stretch as indicated at Table II runs 2 to 6. Each film sample is then annealed at 90° C. for 10 seconds at constant length. The resulting biaxially stretched microporous film samples are then tested and the results summarized at Table II.

TABLE I

|  | Soltex G 60-42 (Polyethylene) | 650-F4 (Polyethylene) |
|---|---|---|
| Density (gm/cc) | 0.960 | 0.960 |
| Melt Index (ASTM D-1238) | 0.42 | 5.5 |
| Gel Count[1] | 0 | 1 |
| $\overline{M}_w$[2] | 71,100 | 50,315 |
| $\overline{M}_n$[3] | 15,200 | 7,472 |
| MWD[4] | 4.7 | 6.73 |
| Crystallization time (seconds) at 120° C. | ND | 67 |

[1]Gels counted visually over 90 in² area in extruded 3 mil precursor film.
[2]$\overline{M}_w$ = weight average molecular weight which can be determined by gel permeation chromotography using O-dichloro-benzene at 145° C. which is further discussed in J.F. Johnson and R.F. Porter, eds., "Analytical Gel Permation Chromotography" Wiley Interscience N.Y. (1968), the disclosure of which is herein incorporated by reference.
[3]$\overline{M}_n$ = number average molecular weight which can be determined by end group analysis as discussed in 9 Encyclopedia of Polymer Science and Technology 184, Interscience Publishers (1967), the disclosure of which is herein incorporated by reference.
[4]MWD = molecular weight distribution ratio = $\overline{M}_w/\overline{M}_n$.

TABLE II

| Run No. | Film Processing Description | Gurley, sec. | Gurley sec./mil of stretched film thickness | Film Guage mil | Porosity[1] % | Pore[2] Size, (μ) | Surface[3] Area, m²/gm |
|---|---|---|---|---|---|---|---|
| 1 | Solvent Stretch — (300% MD) | 4.3 | 1.9 | 2.2 | 55.0 | 1.00 × 0.33 | ND |
| 2 | Solvent Stretch — (300% MD) + 50% XMD | 1.0 | .53 | 1.9 | 65.9 | 0.96 × 0.99 | 16.0 |
| 3 | Solvent Stretch — (300% MD) — 100% XMD | 0.9 | .53 | 1.7 | 65.4 | 0.55 × 0.80 | 23.1 |
| 4 | Solvent Stretch — (300% MD) + 150% XMD | 0.7 | .54 | 1.3 | 71.1 | 0.27 × 0.81 | 24.6 |
| 5 | Solvent Stretch — (300% MD) + 200% XMD | 0.7 | .7 | 1.0 | 72.2 | ND | 34.8 |
| 6 | Solvent Stretch — (300% MD) + 250% XMD | 0.6 | .67 | 0.9 | 77.9 | ND | ND |

ND = not determined
MD = machine direction
XMD = cross machine direction
[1]% Porosity determined as described herein.
[2]Average pore size determined from electron micrographs as described herein.
[3]Surface area is determined as described herein.

As may be seen from the results of Table II, the Gurley values per mil of film thickness decreases up to between 50 and 100% stretch in the cross machine direction and then begins to increase. The porosity and surface area also increases as the degree of stretch in the cross machine direction in increased. In addition the pore shape changes from elliptical in the machine direction to about equal pore size in the machine and cross machine direction at a stretch between 50 and 100% in the cross machine direction. As the degree of stretch is increased above 100% the pore size in the cross machine direction is greater than in the machine direction. This change in shape is accompanied by a slight reduction in the permeability, i.e., increase in Gurley.

EXAMPLE 2

Example 1 is repeated with the exception that the precursor film thickness is 3 mil, certain processing conditions are varied and different tests are conducted on the film samples as indicated at Table III runs 1 to 8.

As may be seen from the data presented at Table III, the Gurley per mil of thickness of the biaxially stretched microporous film is increased i.e., the Gurley value is decreased, as the degree of stretch in the cross machine direction is increased between 50 and 100% stretch and then gradually decreases. The balance of burst strength and tensile strength is also optimized at a degree of cross machine stretch of between 50 and 100%.

TABLE III

| Run No. | Film Processing Description | Gurley sec. | Film Guage mil | Gurley sec./mil of stretched film thickness | Porosity % | Burst Strength Mullen Pts. | Tensile Strength (psi) MD | Tensile Strength (psi) XMD | Tensile Strength Ratio of MD/XMD |
|---|---|---|---|---|---|---|---|---|---|
| 1 | Precursor film | ND | 2.7 | ND | ND | 29.1 | 4080 | 5190 | 0.8 |
| 2 | Solvent Stretched (300% MD) | 4.3 | 2.2 | 1.9 | 64 | 17.0 | 4540 | 950 | 4.8 |

TABLE III-continued

| Run No. | Film Processing Description | Gurley sec. | Film Guage mil | Gurley sec./mil of stretched film thickness | Porosity % | Burst Strength Mullen Pts. | Tensile Strength (psi) MD | Tensile Strength (psi) XMD | Tensile Strength Ratio of MD/XMD |
|---|---|---|---|---|---|---|---|---|---|
| 3 | Solvent Stretched (300% MD) + 50% XMD | 1.0 | 1.9 | .53 | 65.9 | 13.7 | 1010 | 1120 | 0.9 |
| 4 | Solvent Stretched (300% MD) + 100% XMD | 0.9 | 1.7 | .53 | 65.4 | 12.6 | 2400 | 1920 | 1.2 |
| 5 | Solvent Stretched (300% MD) + 150% XMD | 0.7 | 1.3 | .54 | 71.1 | 10.6 | 1820 | 2220 | 0.8 |
| 6 | Solvent Stretched (300% MD) + 200% XMD | 0.7 | 1.0 | .70 | 72.2 | 6.9 | 1750 | 1680 | 1.1 |
| 7 | Solvent Stretched (300% MD) + 250% XMD | 0.6 | 1.0 | .60 | 77.9 | 8.5 | 1710 | 1580 | 1.1 |
| 8 | Solvent Stretched (300% MD) + 300% XMD | 0.5 | 0.9 | .55 | 71.7 | 7.2 | 1200 | 2570 | 0.5 |

ND = not determined
MD = machine direction
XMD = cross machine direction
Tensile Strength determined by ASTM D - 882 - method A (sample width 15mm).
Burst Strength determined by ASTM D - 774
Porosity determined as described herein.

EXAMPLE 3

Example 1 is repeated with the exception that the precursor film thickness is 6 mils, certain processing conditions are varied and different tests are conducted on the film samples as indicated at Table IV. The Gurley values per mil of film thickness again peaks at a degree of stretch in the cross machine direction between 50 and 100%. The data also illustrates that the balance of tensile strength in both directions of stretch becomes more equal as the degree of stretch is increased even when using thicker films of 6 mils.

TABLE IV

| Run No. | Film Processing Description | Gurley sec. | Film Guage mil | Gurley sec./mil of stretched film thickness | Tensile Strength (psi) MD | Tensile Strength (psi) XMD | Tensile Strength Ratio of MD/XMD |
|---|---|---|---|---|---|---|---|
| 1 | Solvent Stretched (300% MD) | 2.9 | 4.1 | .71 | 3890 | 995 | 3.9 |
| 2 | Solvent Stretched (300% MD) + 25% XMD | 1.4 | 2.9 | .48 | 4270 | 900 | 4.7 |
| 3 | Solvent Stretched (300% MD) + 50% XMD | 1.6 | 3.8 | .42 | 2710 | 1170 | 2.3 |
| 4 | Solvent Stretched (300% MD) + 70% XMD | 1.5 | 4.0 | .37 | 2420 | 1330 | 1.8 |
| 5 | Solvent Stretched (300% MD) + 96% XMD | 1.3 | 3.5 | .37 | 1920 | 1230 | 1.6 |
| 6 | Solvent Stretched (300% MD) + 150% XMD | 1.2 | 2.1 | .57 | 1330 | 1710 | 0.8 |

MD = machine direction
XMD = cross machine direction
Tensile Strength determined by ASTM D 882 - method A (sample width 15mm)

EXAMPLE 4

Example 1 is repeated with the exception that the precursor film thickness is 3 mils, a tenter frame is employed to achieve transverse stretching and the strain rate employed for "solvent stretching" is 50%/min. The degree of transverse stretch as well as appropriate tests and test results are summarized at Table V as runs 1 to 4. The data of Table V illustrates the decrease in Gurley values per mil of film thickness which results from stretching in the machine direction. The increase in surface area with increasing stretch in the machine direction is also illustrated.

TABLE V

| Run No. | Film Processing Description | Gurley sec. | Film Guage mil | Gurley sec./mil of stretched film thickness | Porosity % | Surface Area m²/gm |
|---|---|---|---|---|---|---|
| 1 | Solvent Stretch (300% MD) | 1.8 | 2.0 | .90 | 56 | 13.6 |
| 2 | Solvent Stretch (300% MD) + 50% XMD | 0.7 | 1.8 | .39 | ND | 17.5 |
| 3 | Solvent Stretch (300% MD) + 75% XMD | 0.7 | 1.7 | .41 | ND | 20.8 |
| 4 | Solvent Stretch (300% MD) + 100% XMD | 0.6 | 1.7 | .35 | ND | 23.3 |

MD = machine direction
XMD = cross machine direction
% Porosity determined as described herein
Surface area determined as described herein

EXAMPLE 5

Example 4 is repeated with the exception that certain processing conditions are varied and different tests are performed as indicated at Table VI. The results of the appropriate tests are summarized at Table VI.

As may be seen from the data of Table VI, the tensile strength ratio approaches unity at a degree of stretch of about 75%. Moreover, the Gurley value is lowest at about 75%. The same general trends illustrated by the previous Examples are evident such as decreased Gurley, improved tensile strength balance and increased surface area.

TABLE VI

| Run No. | Film Processing Description | Gorley sec. | Film Guage mil | Gurley sec./mil of stretched film thickness | Tensile Strength psi MD | Tensile Strength psi XMD | Tensile Strength Ratio of MD/XMD |
|---|---|---|---|---|---|---|---|
| 1 | Solvent Stretched (300% MD) | 1.8 | 2.1 | .85 | 3790 | 1900 | 2.0 |
| 2 | Solvent Stretched (300% MD) + 50% XMD | 0.7 | 1.9 | .37 | 3270 | 2150 | 1.52 |

TABLE VI-continued

| Run No. | Film Processing Description | Gorley sec. | Film Guage mil | Gurley sec./mil of stretched film thickness | Tensile Strength psi MD | Tensile Strength psi XMD | Tensile Strength Ratio of MD/XMD |
|---|---|---|---|---|---|---|---|
| 3 | Solvent Stretched (300% MD) + 75% XMD | 0.6 | 2.0 | .30 | 2630 | 2480 | 1.06 |
| 4 | Solvent Stretched (300% MD) + 100% XMD | 0.7 | 1.7 | .41 | 1290 | 2420 | 0.54 |

MD = machine direction
XMD = cross machine direction
Tensile strength determined by ASTM D 882 Method A (sample width 15 mm)

EXAMPLE 6

Example 4 is repeated with the exception that two different polyethylene polymers are employed, namely, JV040C available from Mitsubishi for runs 1 to 10 and DMDJ 7006 available from Union Carbide Corp. for runs 11 to 29. The appropriate properties of these two polymers are summarized at Table VII. The precursor film is passed through perchloroethylene at 90° C. for a residence time of about 15 seconds at constant length and then "solvent stretched" 300% in the machine direction at a strain rate of 95%/min. for runs 1–10, 66%/min. for runs 11–14, 76%/min. for runs 15–26, and 66%/min. for runs 27–29 while maintaining the temperature of the perchloroethylene swelling agent at 90° C. The solvent stretched film is then passed again through perchloroethylene at 90° C. for a residence time of about 15 seconds and then dried in air at room temperature. The dried film is then transverse stretched. The processing conditions employed for transverse stretching i.e., in the cross machine direction are summarized at Table VIII as are the Gurly values of the uniaxially "solvent stretched" microprous film before and after transverse stretching. The biaxially stretched microporous film is heat set for a period of 1 minute in a hot air oven at the temperatures indicated at Table VIII at constant length in both the machine and cross machine directions of stretch using two sets of rolls rotating at the same peripheral speed to control the tension in the machine direction and the tenter frame to control tension in the cross machine direction.

As may be seen from the data of Table VIII the solvent stretched film prepared from the DMDJ 7006 resin develops splits more frequently then those prepared from the JV040C resin when transverse stretched. This is attributed to the higher gel count of the DMDJ 7006 resin in comparison to the latter resin. The splits which develop in the JV040C resin are also attributed to the presence of gels in this resin. Such splitting may be reduced by filtering the resin in the manner described herein before preparing the precursor film.

TABLE VII

|  | Mitsubishi JV040C Polyethylene | Union Carbide Corp. DMDJ 7006 Polyethylene |
|---|---|---|
| Density (gm/cc) | 0.968 | 0.962 |
| Melt Index | 5.0 | 6.0 |
| [1]Gel Count | 0–53 | 194–225 |
| [2]$\overline{M}_w$ | 60,395 | 49,098 |
| [3]$\overline{M}_n$ | 10,690 | 10,005 |
| [4]MWD | 5.65 | 4.91 |
| Crystallization time at 120° C. (seconds) | 33.6 | 45.5 |

[1]Gels counted visually over 90 in² area in several extruded 3 mil precursor film samples.
[2]$\overline{M}_w$ = weight average molecular weight which can be determined by gel permeation chromatography using o-dichlorobenzene solvent at 145° C. which is further discussed in J.F. Johnson and R.F. Porter, eds., "Analytical Gel Permeation Chromatography" Wiley Interscience N.Y. (1968), the disclosure of which is herein incorporated by reference.
[3]$\overline{M}_n$ = number average molecular weight determined by end group analysis as discussed in 9 Encyclopedia of Polymer Science and Technology 184, Interscience Publishers (1967), the disclosure of which is herein incorporated by reference.
[4]MWD = molecular weight distribution ratio = $\overline{M}_w/\overline{M}_n$

TABLE VIII

| Run No. | Polymer | No. of plys | Thickness of precursor film ply (mil) | M.D. stretched film guage (mil/ply) | Degree of Transverse stretch (%) | Strain Rate of Transverse stretch (%/min) | Transverse stretch Temp. (C.°) | Speed Through Tenter (ft./min) | Heat Set Temp. (C.°) | Gurley, sec. Before Transverse Stretch | Gurley, sec. After Transverse Stretch |
|---|---|---|---|---|---|---|---|---|---|---|---|
| 1 | JV04DC | 1 | 3 | 2.0 | 80 | 50 | RT | 10 | 100 | 2.3 | 0.70 |
| 2 | JV04DC | 1 | 3 | 2.0 | 60 | 75 | RT | 10 | 100 | 2.3 | 1.3 |
| 3 | JV04DC | 1 | 3 | 2.0 | 60 | 75 | RT | 10 | 100 | 2.3 | 0.84 |
| 4 | JV04DC | 1 | 3 | 2.0 | 60 | 37 | RT | 10 | 100 | 2.3 | 0.69 |
| 5 | JV04DC | 1 | 3 | 2.0 | 60 | 75 | 80 | 10 | 100 | sample-split | |
| 6 | JV04DC | 1 | 3 | 2.0 | 50 | 37 | 80 | 10 | 100 | 2.3 | 0.83 |
| 7 | JV04DC | 1 | 3 | 2.2 | 60 | 75 | RT | 10 | 100 | 2.4 | 0.71 |
| 8 | JV04DC | 1 | 3 | 2.2 | 55 | 34 | 60 | 10 | 100 | sample-split | |
| 9 | JV04DC | 1 | 3 | 2.2 | 55 | 68 | 60 | 20 | 100 | 2.4 | 0.98 |
| 10 | JV04DC | 1 | 3 | 2.2 | 35 | 31 | 80 | 40 | 115 | 2.4 | 1.02 |
| 11 | DMDJ7006 | 1 | 3 | 2.1 | 80 | 50 | RT | 10 | 100 | 2.8 | 0.77 |
| 12 | DMDJ7006 | 1 | 3 | 2.1 | 60 | 37 | RT | 10 | 100 | 2.8 | 0.68 |
| 13 | DMDJ7006 | 1 | 3 | 2.1 | 55 | 34 | RT | 10 | 100 | 2.8 | 0.83 |
| 14 | DMDJ7006 | 1 | 3 | 1.1 | 50 | 37 | RT | 10 | 100 | 2.8 | 0.81 |
| 15 | DMDJ7006 | 2 | 1.5 | 1.1 | 55 | 41 | RT | 10 | 100 | sample-split | |
| 16 | DMDJ7006 | 2 | 1.5 | 1.1 | 55 | 68 | RT | 10 | 100 | sample-split | |
| 17 | DMDJ7006 | 2 | 1.5 | 1.1 | 30 | 28 | RT | 10 | 100 | sample-split | |
| 18 | DMDJ7006 | 2 | 1.5 | 1.1 | 35 | 131 | 80 | 40 | 115 | sample-split | |
| 19 | DMDJ7006 | 2 | 1.5 | 1.0 | 70 | 65 | RT | 10 | 10 | sample-split | |
| 20 | DMDJ7006 | 2 | 1.5 | 1.0 | 50 | 47 | RT | 10 | 10 | 2.9 | 1.02 |
| 21 | DMDJ7006 | 2 | 1.5 | 1.0 | 30 | 28 | RT | 10 | 10 | 2.9 | 1.16 |
| 22 | DMDJ7006 | 2 | 1.5 | 1.0 | 75 | 47 | 60 | 10 | 10 | 2.9 | 0.72 |
| 23 | DMDJ7006 | 2 | 1.5 | 1.0 | 55 | 34 | 60 | 10 | 10 | 2.9 | 0.88 |

TABLE VIII-continued

| Run No. | Polymer | No. of plys | Thickness of precursor film ply (mil) | M.D. stretched film gauge (mil/ply) | Degree of Transverse stretch (%) | Strain Rate of Transverse stretch (%/min) | Transverse stretch Temp. (C.°) | Speed Through Tenter (ft./min) | Heat Set Temp. (C.°) | Gurley, sec. Before Transverse Stretch | Gurley, sec. After Transverse Stretch |
|---|---|---|---|---|---|---|---|---|---|---|---|
| 24 | DMDJ7006 | 2 | 1.5 | 1.0 | 55 | 34 | 60 | 10 | 10 | sample-split | |
| 25 | DMDJ7006 | 2 | 1.5 | 1.0 | 35 | 33 | 95 | 10 | 10 | 2.9 | 0.96 |
| 26 | DMDJ7006 | 2 | 1.5 | 1.0 | 35 | 98 | 95 | 30 | 30 | 2.9 | 0.79 |
| 27 | DMDJ7006 | 2 | 1.5 | 1.0 | 45 | 34 | 80 | 10 | 10 | sample-split | |
| 28 | DMDJ7006 | 2 | 1.5 | 1.0 | 35 | 33 | 80 | 10 | 10 | sample-split | |
| 29 | DMDJ7006 | 2 | 1.5 | 1.0 | 35 | 131 | 80 | 40 | 40 | 2.7 | 1.05 |

RT = Room Temp. = 25° C.
JV04DC - available from Mitsubishi (see Table VII)
DMDJ7006 - available from Union Carbide Corp. (see Table VII).

EXAMPLE 7

Example 4 employing a tenter frame is repeated with a precursor film which has been annealed at 90° C. at constant length for 96 hrs and which has a film thickness of 3 mil, with the exception that certain processing conditions are varied and different tests are conducted on the biaxially stretched microporous film as illustrated at Table IX.

Some of the samples were allowed to shrink during the drying step after solvent stretching in the machine direction as indicated in the "dry-box relax" column. Typically drying is conducted at constant length. Some of the solvent stretched film samples were relaxed in an attempt to reduce the internal strains of the film and thereby reduce the tendency of the film to split when transversed stretched. The overall stretch level identifies the total degree of stretch in the machine direction after relaxation, if employed.

The strain rate in the machine direction of solvent stretch is between 65 and 125%/min at a solvent stretch temperature of 90° C., and the strain rate in the cross machine direction of stretch is varied between 119 and 312%/min at room temperature as shown in Table IX.

As may be seen from the data of Table IX uniaxially solvent stretched microporous film having Gurley values not less than about 2.0 seconds per mil thickness of film generally split when stretched in a travsverse direction. The relaxation after drying showed little benefit toward reducing splitting.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. In a process for preparing an open-celled microporous film by (1) contacting a non-porous precursor film having both an amorphous component and a crystalline component with a swelling agent comprising a non-aqueous solvent having a Hildebrand solubility parameter at or near that of the precursor film, for a time sufficient to permit adsorption of the swelling agent into the film, (2) stretching said precursor film in at least one direction while in contact with the swelling agent, and (3) removing said swelling agent while maintaining said film in its stretched state the improvement which comprises:

(a) providing said precursor film from an olefin homopolymer or mixtures thereof characterized by a balance of properties of density, melt index, molecular weight distribution ratio ($M_w/M_n$), crystallization time, and a average gel count, sufficient to impart to the non-porous precursor film the potential to develop a Gurley value of less than about 2

TABLE IX

| Run No. | Solvent Stretch % | Dry Box Relaxed % | MD Overall Stretch % | MD Strain Rate %/min | MD Stretched film Gauge mil | MD Stretched film Gurley sec. | Gurley sec./mil of MD Stretched film thickness | XMD Stretch % | XMD Strain Rate %/min | XMD Stretched film Gauge mil | Porosity % | XMD Stretched film Gurley sec. |
|---|---|---|---|---|---|---|---|---|---|---|---|---|
| 1 | 257 | 0 | 257 | 65 | 2 | 10.0 | 5.0 | 70 | 119 | Splits | No Sample | |
| 2 | 300 | 0 | 300 | 150 | 2 | 9.4 | 4.7 | 70 | 179 | Splits | No Sample | |
| 3 | 300 | 43 | 257 | 125 | 2 | 10.0 | 5.0 | 70 | 119 | Splits | No Sample | |
| 4 | 257 | 0 | 257 | 65 | 2 | 4.8 | 2.4 | 70 | 260 | Splits | No Sample | |
| 5 | 300 | 0 | 300 | 75 | 2 | 4.0 | 2.0 | 70 | 119 | Splits | No Sample | |
| 6 | 300 | 43 | 257 | 115 | 2 | 4.3 | 2.1 | 70 | 179 | 1.4 | 64 | 1.6 |
| 7 | 300 | 0 | 300 | 65 | 2 | 1.7 | .85 | 70 | 119 | 1.7 | 72 | 0.4 |
| 8 | 300 | 43 | 257 | 60 | 2 | 1.9 | .95 | 70 | 119 | 1.5 | 72 | 0.5 |
| 9 | 300 | 88 | 212 | 75 | 4 | 2.8 | 0.70 | 70 | 119 | 3.9 | 80 | 0.7 |
| 10 | 300 | 88 | 212 | 75 | 4 | 2.8 | 0.70 | 100 | 173 | 3.9 | 71 | 0.8 |
| 11 | 300 | 88 | 212 | 75 | 4 | 2.8 | 0.70 | 125 | 217 | 3.9 | 76 | 0.6 |
| 12 | 300 | 88 | 212 | 75 | 4 | 2.8 | 0.70 | 180 | 312 | 3.7 | 79 | 0.6 |

XMD = Cross machine direction
MD = Machine direction
Porosity determined as described herein.

seconds per mil of film thickness when stretched in a uniaxial direction in accordance with step (b);

(b) unaxially stretching the precursor film of (a) while in contact with the swelling agent under conditions of degree of stretch, strain rate, temperature, and precursor film thickness which are controlled in a manner sufficient to yield a uniaxially stretched microporous film having a Gurley value of less than 2.0 seconds per mil of film thickness; and (c) transverse stretching the microporous film of (b) in a direction perpendicular to the uniaxial direction of stretch to increase the permeability of the microporous film of (b) without causing splitting of the resulting biaxially stretched microporous film.

2. The process of claim 1 wherein the olefin homopolymer is polyethylene having a melt index of from about 3 to about 20, a molecular weight distribution ratio of from about 3.8 to about 13, and a density of from about 0.960 to about 0.965 gm/cc, and wherein the precursor film is pre-soaked in the swelling agent at the stretching temperature of (b) for a period of about 10 seconds to about 10 minutes at constant length.

3. The process of claim 2 wherein the swelling agent is perchloroethylene and the solvent stretch temperature of (b) is from about 80° to about 90° C.

4. The process of claim 3 wherein the precursor film is prepared by a blown film extrusion method and has a thickness of from about 0.75 to about 12 mils.

5. The process of claim 3 wherein the precursor film is prepared by a slit die extrusion method and has a thickness of from about 0.75 to about 15 mils.

6. The process of claim 3 wherein uniaxial stretching is conducted at a degree of stretch of from about 70 to about 300% and a strain rate of from about 5 to about 100%/minute and the uniaxially stretched film is post-soaked in swelling agent at a temperature of about 70° to about 90° C. at substantially constant length for a period of about 10 seconds to about 10 minutes.

7. The process of claim 3 wherein uniaxial stretching is conducted at a degree of stretch of about 300% and a strain rate of about 15%/minute.

8. The process of claim 1 wherein the uniaxial stretching is conducted in a manner sufficient to yield a uniaxially stretched microporous film having a Gurley value of less than about 1.8 seconds per mil of film thickness.

9. The process of claim 1 wherein the uniaxially stretched microporous film is dried at substantially constant length prior to transverse stretching to remove the swelling agent.

10. The process of claim 1 wherein the uniaxially stretched microporous film is transverse stretched using a tenter frame.

11. The process of claim 1 wherein the uniaxially stretched microporous film is transverse stretched on a frame which allows shrinkage in the direction of uniaxial stretch.

12. The process of claim 1 wherein the biaxially stretched microporous film of (c) is annealed at a temperature of from about 80° to about 140° C. for a period of about 0.1 second to about 1 hour under conditions such that the film can shrink in either direction of stretch to only a controlled extent not greater than about 15% based on the original linear dimensions of the biaxially stretched microporous film prior to annealing.

13. The process of claim 1 wherein transverse stretching is conducted at a degree of stretch of about 25 to about 200%, a strain rate of about 20 to about 100%/minute and a temperature of about 25° to about 100° C.

14. In a process for preparing an open-celled microporous film by (1) contacting a non-porous precursor film having both an amorphous component and a crystalline component with a swelling agent comprising a non-aqueous solvent having a Hildebrand solubility parameter at or near that of the precursor film, for a time sufficient to permit adsorption of the swelling agent into the film, (2) stretching said precursor film in at least one direction while in contact with the swelling agent, and (3) removing said swelling agent while maintaining said film in its stretched state the improvement which comprises:

(a) providing said precursor film from a homopolymer of polyethylene or mixtures thereof characterized by a melt index of from about 3 to about 20, a density of not less than about 0.960 gm/cc, a molecular weight distribution ratio ($\overline{M}_w/\overline{M}_n$) of from about 3.8 to about 13, an average gel count of not greater than about 2.0 per 90 square inches of precursor film area and a crystallization time at 120° C. of less than about 70 seconds;

(b) uniaxially stretching the precursor film of (a) having a thickness of from about 0.75 to about 15 mils, while in contact with the swelling agent, at a degree of stretch of from about 70 to about 300%, a strain rate of from about 5 to about 100%/minute, and a temperature of from about 80° to about 95° C. to yield a uniaxially stretched microporous film having a Gurley value of not less than about 2 seconds per mil of film thickness; and (c) transverse stretching the microporous film of (b) in a direction perpendicular to the uniaxial direction of stretch to increase the permeability of the microporous film of (b) without causing splitting of the resulting biaxially stretched microporous film.

15. The process of claim 14 wherein the precursor film is uniaxially stretched to yield a uniaxially stretched microporous film having a Gurley value of less than about 1.0 second per mil of film thickness.

16. The process of claim 14 wherein the precursor film is pre-soaked in the swelling agent at substantially constant length at the solvent stretching temperature for a period of from about 10 seconds to about 10 minutes, and the uniaxially stretched film of (b) is post-soaked in the swelling agent at a temperature of about 70° to about 90° C. at substantially constant length, dried to evaporate the swelling agent and cooled to room temperature prior to transverse stretching.

17. The process of claim 14 wherein the molecular weight distribution ratio of the polyethelene homopolymer is from about 6 to about 12.

18. The process of claim 14 wherein the molecular weight distribution ratio of the polyethylene homopolymer is from about 8 to about 12.

19. The process of claim 17 wherein the density of the polyethylene homopolymer is from about 0.960 to about 0.965 gm/cc.

20. The process of claim 18 wherein the density of the polyethylene homopolymer is from about 0.962 to about 0.965 gm/cc.

21. The process of claim 16 wherein the average gel count of the polyethylene homopolymer is from about 0 to about 2.0 per 90 square inches of precursor film area and the crystallization time of said homopolymer at 120° C. is from about 10 to about 40 seconds.

22. The process of claim 21 wherein the swelling agent is perchloroethylene and the solvent stretch temperature is from about 80° to about 95° C.

23. The process of claim 22 wherein uniaxial stretching is conducted at a degree of stretch of about 300%, a strain rate of about 5 to about 20%/minute, and at a temperature of about 90° to about 95° C.

24. The process of claim 22 wherein uniaxial stretching is conducted at a degree of stretch of about 300%, a strain rate of about 15%/minute and a temperature of about 90° C.

25. The process of claim 14 wherein transverse stretching is conducted at a degree of stretch of about 25 to about 200%, a strain rate of about 20 to about 100%/minute and a temperature of from about 25° to about 100° C.

26. The process of claim 14 wherein transverse stretching is conducted at a degree of stretch of from about 60 to about 150%, a strain rate of about 75 to about 100%/minute, and a temperature of about 25° C.

27. The process of claim 14 wherein the biaxially stretched microporous film is annealed at a temperature of from about 80° to about 140° C. for a period of about 0.1 second to about 1 hour under conditions such that the film can shrink in either direction of stretch to only a controlled extent not greater than about 15% based on the original linear dimensions of the biaxially stretched microporous film prior to annealing.

* * * * *